United States Patent [19]

Wilson et al.

[11] Patent Number: 4,560,557
[45] Date of Patent: Dec. 24, 1985

[54] SILICON AND SULFUR STEROIDS AS IRREVERSIBLE INHIBITORS OF HORMONE BIOSYNTHESIS

[75] Inventors: Stephen R. Wilson, Chatham, N.J.; W. Orme-Johnson, Cambridge; A. Nagahisa, Jamaica Plain, both of Mass.

[73] Assignee: University Patents, Inc., Westport, Conn.

[21] Appl. No.: 550,676

[22] Filed: Nov. 10, 1983

[51] Int. Cl.[4] ............................................. A61K 31/56
[52] U.S. Cl. ................................... 514/178; 260/397.2
[58] Field of Search ...................... 260/397.2; 424/238

[56] References Cited

PUBLICATIONS

Chem. Abstracts, vol. 100, No. 11, Par. 81879(b) (1984).
Chem. Abstracts, vol. 96, No. 23, Par. 198,662(a).
CA-vol. 96, No. 23, Par. 198,662(r), Journ. Org. Chem., 1982, vol. 47, pp. 1983-1984, by Wilson et al.

Primary Examiner—Elbert L. Roberts
Attorney, Agent, or Firm—George M. Yahwak

[57] ABSTRACT

The compounds of the present invention are irreversible and highly selective inhibitors of the cytochrome P-450 cholesterol side chain cleavage (P-450scc) enzyme responsible for the first and rate limiting step of steroid hormone biosynthesis by the adrenal glands.

8 Claims, 5 Drawing Figures

SILICON AND SULFUR STEROIDS AS IRREVERSIBLE INHIBITORS OF HORMONE BIOSYNTHESIS

The Government has rights in this invention pursuant to grant Number NIH-5-R01-GM28358-03 awarded by the Department of Health and Human Services.

A class of enzyme inactivators, called suicide enzyme inactivators or mechanism-based inactivators, was first described by Konrad Bloch and his collaborators at Harvard University in 1970. These suicide enzyme inactivators are relatively inert molecules which so closely resemble the natural substrate of a specific enzyme that they are structurally indistinguishable from the natural substrate by the enzyme's active site. By interaction with the enzyme at its active site, the inactivator is chemically modified, connecting the inactivator to a reactive compound which then reacts with the target enzyme leading to enzyme inactivation. The initial chemical interaction between inactivator and enzyme is exactly the same as that which occurs between the natural substrate and the enzyme in the normal enzyme catalyzed process; the only difference is that by acting on the suicide substrate, the target enzyme catalyzes its own destruction.

An important and distinctive property of suicide substrates which makes them useful for control of biological processes, is that they are chemically non-reactive—the reactive inactivators are only generated at the active sites of the enzymes, and therefore non-specific reactions with other than the targeted enzymes do not normally occur. Suicide enzyme substrates are therefore highly selective and bring about irreversible inactivation of the target enzyme—properties which are beneficial for compounds exhibiting the pharmacological potential of the substrates of the present invention.

The compounds of the present invention are irreversible and highly selective inhibitors of the cytochrome P-450 cholesterol side chain cleavage enzyme (P-450scc) responsible for the first and rate limiting step of steroid hormone biosynthesis by the adrenal glands, i.e. adrenal steroidogenesis. The ADRENAL GLAND, the site of steroid hormone bio synthesis, is composed of two separate endocrine glands, the adrenal cortex and the adrenal medulla. The adrenal cortex in the adult is divided into a mineral-corticoid secreting and a glucocorticoid secreting portion. An outer zone, the zone glomerulosa, contains the enzymes required for the synthesis of aldosterone, the major mineral-corticoid. The two innermost zones, the zona fasciculata and the zona reticularis, contain the 17-hydroxylase enzymes for synthesizing corticosterone, cortisol and the sex hormones by lack the enzymes for aldosterone production. The specific cells that constitute the zone fasciculata produce cortisol and demonstrate an increase in cAMP synthesis and cortisol output with ACTH stimulation. The exact cellular events following activation of membrane-bound adenylate cyclase that ultimately lead to steroidogenesis are not well defined.

Steroid hormone biosynthesis begins with cholesterol which supplies the steroid nucleus. The first step in this overall synthesis of steroid hormones occurs in the mitochondria where the specific enzyme complex cholesterol desmolase (DESM) catalyzed the cleavage of the cholesterol side chain and the sequential hydroxylation steps to form pregnenolone. This product diffuses to the endoplasmic reticulum where the isomerase, 17-hydroxylase (17-OH) and 21-hydroxylase (21-OH) enzymes complete the synthesis of various hormonal intermediates for the glucocorticoid and sex hormones. Movement back to the mitochondria, where the 11-hydroxylase (11-OH) enzyme is localized, completes the synthesis of cortisol, which is the major glucocorticoid in man. A simplified scheme for adrenal steroidogenesis is depicted in the following scheme:

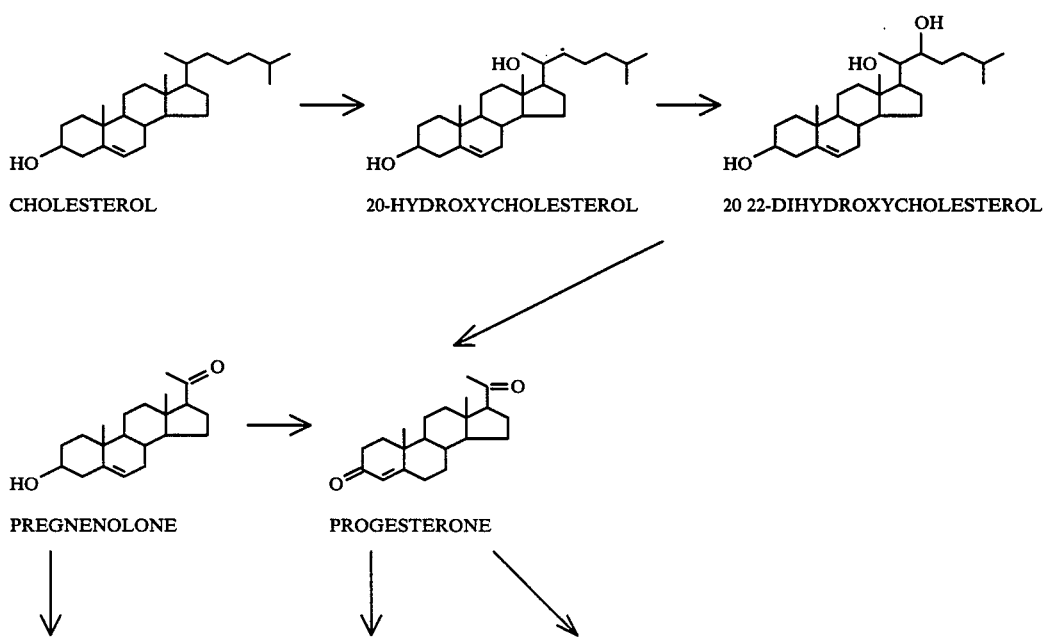

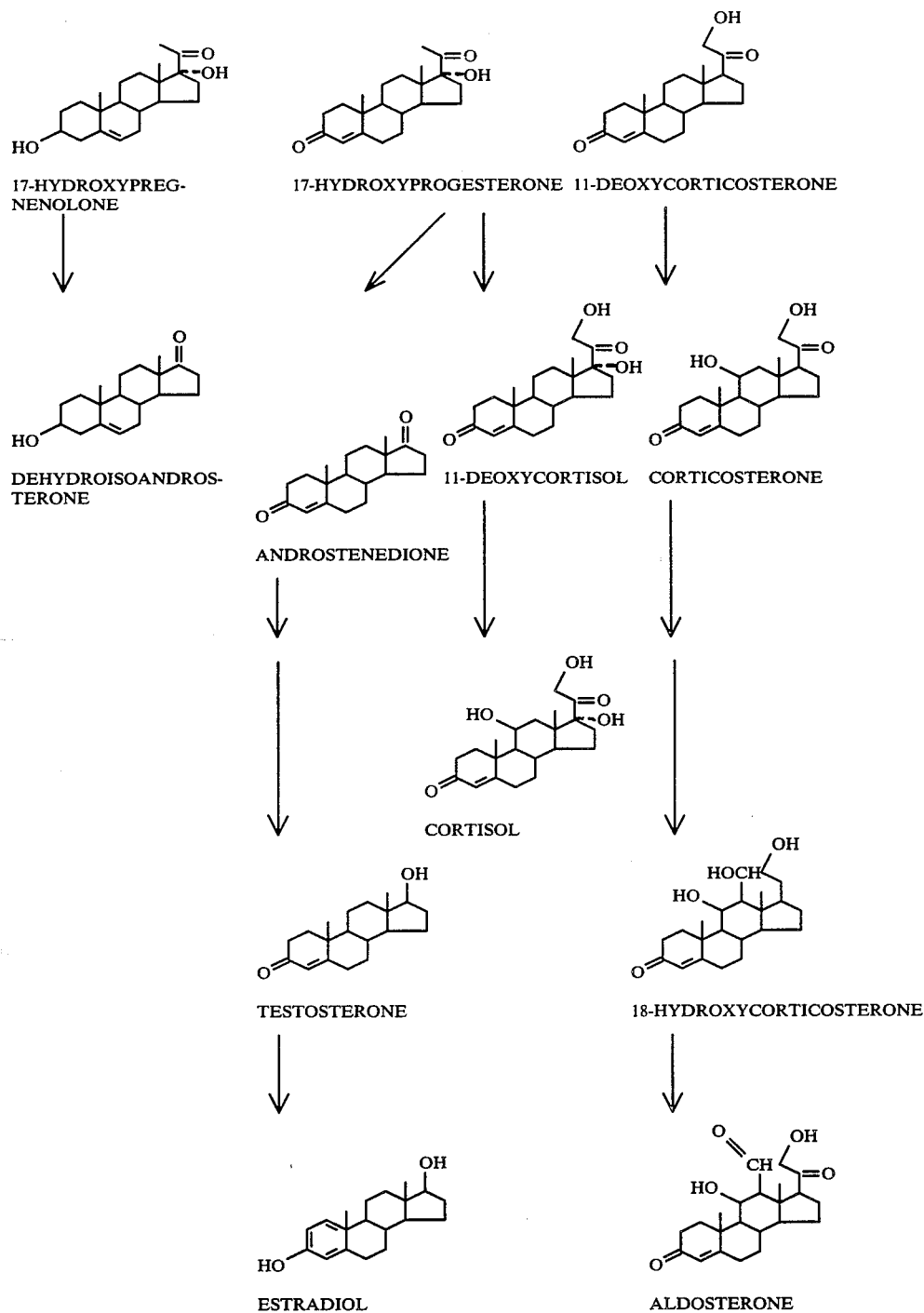
A simplified scheme of the stages of hormone synthesis within the subcellular structures of the adrenal gland cell is depicted in the following scheme:

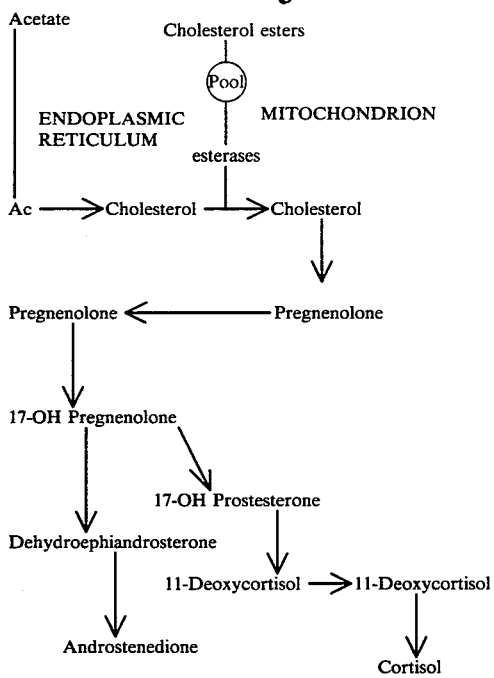

Although Cortisol, i.e. hydrocortisone, is only one of more than 40 corticosteroids produced by the body, it comprises 90 percent or more (approximately 20-25 mg per day is synthesized and released in response to adrenocorticotropin - ACTH secreted by the anterior pituitary gland) of the total adrenal steroids.

In the normal individual, plasma cortisol concentrations demonstrate a diurnal variation. Starting shortly after midnight, the plasma cortisol concentration increases, reaches a peak at about 8 a.m. and then follows a gradually diminishing course that reaches its lowest ebb in the late evening. Samples drawn in the early morning and late afternoon are useful in documenting this pattern that is lost in certain adrenal abnormalities such as Cushing's syndrome. Cortisol acts to promote gluconeogenesis in the liver especially by enhancing the conversion of amino acids to glucose. It also affects glucose metabolism by reducing insulin secretion and increasing glucagon release by pancreatic alpha cells. The increase in blood glucose concentration results from an accumulation of glucose precursors made available to the liver from muscle and adipose tissue and an activation of the liver enzymes responsible for gloconeogenesis and amino transfer.

An increase in the size of the amino acid pool is a result of an overall catabolic effect that cortisol produces on protein metabolism. This is followed by deamination and conversion to carbohydrate. Other biologic effects of cortisol include a decrease in glucose utilization in muscle, inhibition of protein anabolism, and an inhibition of the basic processes of the inflammatory responses associated with infection. Maintenance of blood pressure within normal limits is a function of cortisol because of the potentiation effects it has on norepinephrine. Cortisol also influences other endocrine organs. Cortisol inhibits the enzymatic conversion of epinephrine from norepinephrine and has an effect on the growth hormone and TSH secretions by the pituitary.

Further biological effects of this adrenal steroid hormone are tabulated in the following table.

TABLE I

Metabolic functions and other principal biologic effects of cortisol

5  Increases gluconeogenesis in liver; activation of hepatic enzymes involved in amino acid metabolism
   Increases uptake of amino acids in liver
   Decreases protein synthesis and glucose utilization in muscle, adipose and lymphoid tissues
10 Increases degradation of protein in peripheral tissues
   Reduces insulin secretion
   Increases glucagon release
   Inhibits inflammatory associated reactions
   Depresses immune response
15 Inhibits enzymatic conversion of epinephrine to norepinephrine
   Increases blood pressure in circumstances of stress or shock (i.e., when blood pressure is low).

Thus, in this one instance, by blocking the initial step in cortisol synthesis, i.e. the side chain envelope of cholesterol, one can control, at least in part, the biological effects produced by this major adrenal hormone.

Utilizing the generalized functions of adrenal hormones outlined in Table I, one can gather that the conditions capable of treatment with the compounds of the present invention are varied. They can, in fact, involve any of the myriad of conditions involving elevated levels of steroid hormones which are essentially constant, or which may only be temporary surges resulting from cyclic biological functions. Thus, these inhibitors have the capability of being used for the treatment of hyperestrogenemia which may precede myocardial infarction, or in conditions such as gynecomastia, or in treating male infertility associated with elevated estrogen-induced oligospermia.

The compounds of the present invention are also potentially useful in fertility control where they would be effective in reducing estrogen surges observed in various stages of ovulation. In addition, since estrogen synthesis is necessary for implantation of fertilized ova in humans (as well as in many other species) post-coital administration of these inhibitors has the potential of preventing implantation of the fertilized ova, and therefore acting as a "morning after" pharmaceutical. Administration of these inhibitors should also provide a means of regulating the mating behavior in the males of many domestic pets which finds its control in the fluctuation of sexual steroidal hormones.

There is a great deal of basic and clincal data which suggests human breast cancers are divided into hormone-dependent and hormone-independent subtypes. Clinical and biochemical data suggest that one-third of human to tumors are hormone-dependent, and thus of the 110,000 new cases of breast carcinoma diagnosed in the United States each year, approximately 35,000 can be considered as hormonal-dependent. A variety of data suggest that estrogen is the major hormonal stimulus for growth of the hormone-dependent type of breast carcinoma, and in many instances an ovariectomy, adrenalectomy, or hypophysectomy is commonly performed in patients undergoing a mastectomy to decrease the production of estrogen. Consequently, it is logical to consider the suicide enzyme inhibitors of the present invention as potentially playing a key role in the treatment and pathogenesis of hormone-dependent breast cancer.

Other cancers have also been shown to be hormone-dependent. Endometrial cancer has been related to the presence of excessive endogenous or exogenous estrogen; gonadal and trophoblastic tumors cause somatic hyperestrogenization in humans (which results in varying degrees of feminization in males, and in females, depending upon age, results in symptoms from precocious pseudopuberty to abnormalities of menses to postmenopausal bleeding). Inhibitors, according to the present invention, have potential use in adjunctive therapy in the conservative management of patients with such tumors, since administration of such compounds will reduce the somatic expression of increased estrogen biosynthesis.

Reviews of suicide substrates may be found in *Annual Reports in Medicinal Chemistry,* Section VI—Topics in Chemistry and Drug Design, Chapter 26 (Academic Press, 1982); and *Tetrahedron* Report Number 124, pgs 871 to 909 (1982).

The irreversible inhibitors of the cytochrome P-450 cholesterol side chain cleavage (P-450scc) enzyme responsible for the first and rate-limiting step in steroid hormone synthesis are compounds of the general formula:

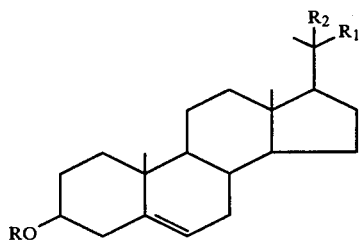

wherein $R_2$ is hydrogen or hydroxyl, $R_1$ is S-$R_3$ or $CH_2CH_2 Si(R_4)_3$. In those side chains containing sulfur, $R_3$ may be a $C_{1-6}$ straight chain alkyl radical, a $C_{1-6}$ straight chain alkylene radical such as —$CH_2$—CH=$CH_2$, or a $C_{3-6}$ branched chain alkyl such as —$CH_2$—$CH_2$—$CH(CH_3)_2$. In those side chains containing silicon, $R_4$ may be hydrogen, hydroxyl, $C_{1-6}$ branched or straight chain alkyl radicals, or mixtures thereof. For optimum activity, however, it is preferred that at least two of the $R_4$ substituents should not be larger than methyl substitutions. In both the sulfur and silicon containing inhibitors, R may be hydrogen, $CH_3$, —$PO(O^-)_2$, or other groups known to be present in P-450scc substrates; rings A and B of the steroid molecule, in fact, may be modified to include those groups known to be present in known P-450scc substrates.

The cholesterol side chain cleavage (p-450scc) inhibitors of the present invention all have in common the unusual feature of either the C-22 carbon of the normally accepted P-450scc substrate being replaced by a sulfur atom, or of containing a substituted silyl group in the side chain. The compounds of the present invention are optically active and possess the natural steroid chemistry. While only the natural isomers, that is those with the angular methyl groups at C-10 and C-13, are thought to be the most active inhibitors, mixtures of these compounds with their optical antipodes are also included within the scope of this invention. Active compounds of the sulfur-containing side chain possess the 20S configuration.

Compounds according to the present invention may be synthesized from known steroid precursors, either steroids derived from natural sources, or synthetic or semi-synthetic steroids.

More particularly, with specific regard to the side chain silyl steroids of the present invention, these are compounds having the formulae:

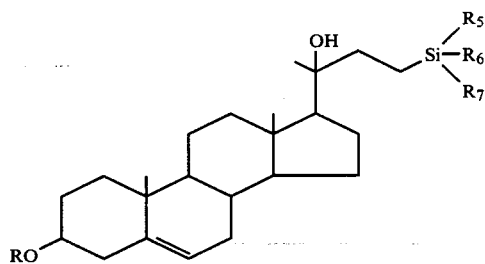

where $R_5$, $R_6$, and $R_7$ are hydrogen, lower alkyls of 1–6 carbon atoms, or mixtures of the same; and R, although commonly hydrogen, may be $CH_3$, —$PO(O^-)_2$ or any other group known to be present in substrates of P-450scc.

Included in the scope of the silicon portion of the present invention are the novel Grignard intermediates.

$$X\ Mg—CH_2—CH_2—Si\ (R_4)_3$$

wherein $R_4$ are as defined above and wherein X is a halogen atom, which intermediates are used to prepare the P-450scc inhibitors as defined.

The following syntheses are illustrative of the (trisubstituted) silyl side chain compound of the present invention (analogous reactions may be effected with other ring A/B analogs).

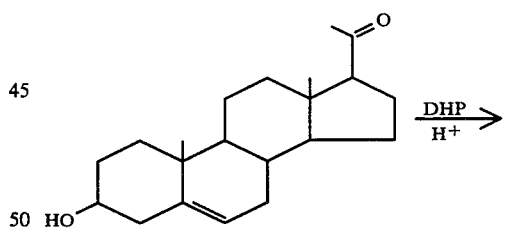

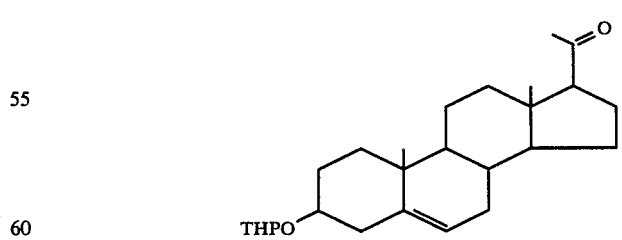

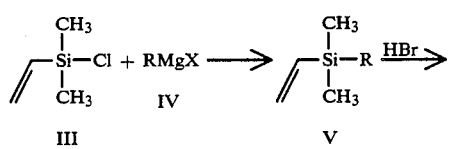

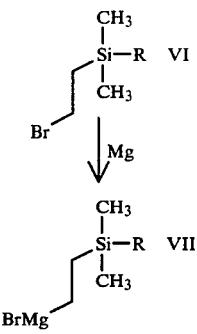

In these generalized syntheses, either pregnenolone (I) or a substituted protected pregnenolone (II), wherein THP is one of many of the known common blocking/protecting groups which may be used as an intermediate reagents in the present invention, is reacted with a silicon-containing Grignard reagent (VII). These intermediates can readily be made by a modification of the procedure reported in the Journal of Organic Chemistry, volume 47, pages 1984–85 (1982).

Well known vinyl-dimethylchlorosilane (III) (or analogous dialkyl compounds) can be reacted with grignard reagents (IV) to produce vinyl silane (V). The addition of HBr to compound V, catalyzed by benzoyl peroxide or other suitable initiator, gives the bromide of compound VI. The formation of Grignard reagent of compound VII from compound VI is straight forward. Reagents of compound VII react with compound II or in excess with compound I to yield, as the major products, silyl containing compounds of the present invention (or their protected derivatives):

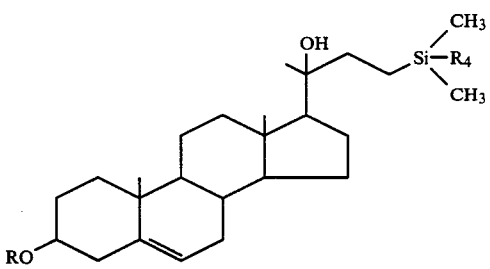

Hydrolysis of the C-3 blocking group in those instances in which the formation of the silyl containing compounds of the present invention have been prepared with compound II, may be carried out in the usual manner with a mild acid and water. The resulting 20-OH group is known to possess the 20(S) configuration.

A more specific detailed description of the (tri-substituted) silyl steroid inhibitor of the present invention is set forth in the following Examples. In some instances, production of the compound of the invention required modification of these examples, and these modifications are set apart from the example by parenthesis. Example I illustrates the preparation of the 23 dimethylethyl silyl-containing compound; Example II illustrates the preparation of the 23 dimethylisopropyl silyl-containing compound; and Example III illustrates the preparation of the 25 trimethyl silyl-containing compound according to the present invention.

EXAMPLE I 1.2 g of dimethyl-vinyl-chlorosilane in 20 ml ether was reacted with 5 ml, 2M ethyl magenesiumbromide in ether at room temperature overnight. Usually work-up and distillation gave 0. g ethyl-dimethylvinyl silane. 0. g ethyl-dimethylvinyl silane was dissolved in 100 ml pentane, and 0.1 g benzoyl peroxide was added. Then anhydrous HBr was bubbled through the solution (for 3 to 4 hours) until all the olefin had reacted. After washing the pentane layer with water, and following concentration, most of the benzoyl peroxide could be removed by crystallization (if necessary, the product was extracted with sodium thiosulfate). The remaining bromide compound was converted directly into the corresponding Grignard. Addition of the calculated amount of pregnenolone, i.e. 2 equivalents (or pregnenonolone-THP, i.e. 1 equivalent) to the ethereal Gignard solution and stirring overnight produced the desired alcohols. Usual work-up in ether/water (or dilute aqueous acid hydrolysis of the THP ether) gave a compound of the invention. The produce was purified by crystallization (or if necessary, by column chromatography on silica gel).

EXAMPLE II 9 mlg dimethyl-isopropyl chlorosilane was reacted with 30 ml 1M vinyl lithium to produce dimethyl-isopropylvinyl silane which was purified by distillation. 1 ml of dimethyl-isopropylvinyl silane in 100 ml pentane containing 0.1 g benzoyl peroxide was allowed to react with HBr ny bubbling the gas through the solution (for 4 to 5 hours). After washing the pentane solution with water to remove excess HBr, and concentration, most of the benzoyl peroxide was recovered by crystallization (if necessary the solution could be washed by sodium thiosulfate solution). The bromide was not further purified, but was coverted with Mg in ether to the corresponding Grignard reagent. Addition of the calculated amount of pregnenolone, i.e. 2 equivalents (or pregnenolone-THP, i.e. 1 equivalent) to this Grignard gave the desired alcohols. Usual work-up (or aqueous hydrolysis/work-up of the THP protected form) gave a compound of the invention.

EXAMPLE III 1.6 g trimethylsilyl ethyl acetate (prepared from trimethylsilyl chloride, ethyl bromoacetate and zinc by the known method) was reduced in ether with lithium aluminum hydride to yield B-trimethylsilyl ethanol. Conversion of the alcohol to the bromide took place with triphenylphosphine and carbon tetrabromide. The bromide was converted to the Grignard in the usual way (Mg/ether) and then the calculated amount of pregnenolone (or pregnenolone-THP) was added. After stirring overnight, and working up in the same was as example I or II gave a compound of the invention.

More particularly, with specific regard to the side chain sulfur steroids of the present invention, these are compounds having the formula

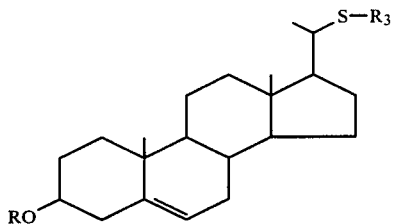

wherein R₃ is a lower alkyl of 1-6 carbon atoms (both straight chain and branched), such as —CH₃ or —CH₂CH₂CH(CH₃)₂, or a lower alkenyl of 1-6 carbon atoms (both straight chain and branched), such as —CH₂—CH=CH₂. R is as previously defined.

The following syntheses are illustrative of the sulfur containing side chain compound of the present invention (analogous reactions may be effected with other ring A/B

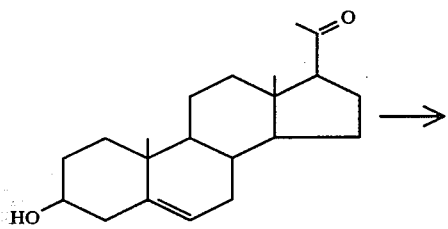

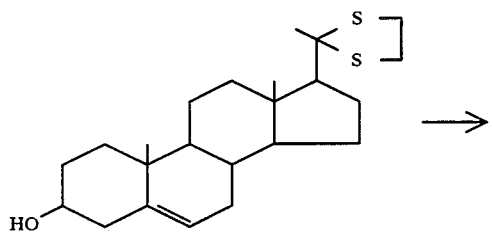

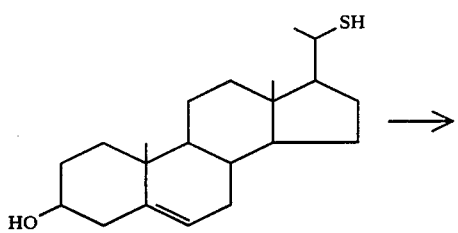

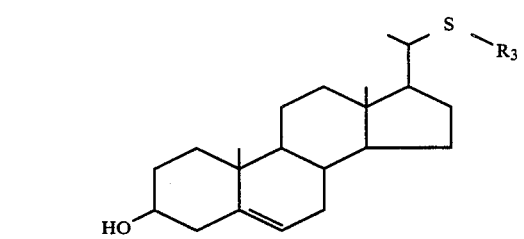

Pregnenolone (or a suitable 3β hydroxy protected derivative) is known to form the thioketal of formula XI with HS CH₂CH₂SH and BF₃.O(Et)₂ (other conditions for this reaction have been reported in the chemical literature). When the thioketal compound is reacted with excess n-butyl lithium, the cleavage/reduction process leads to the appropriate thiol of formula XII (*J. Am. Chem. Soc.*, 102:3577 (1980)). The thiol can then be separated into two fractions by chromatography into a 20R (about 60%) and a 20S (about 40%) compound. The 20S compound, the active isomer, is then alkylated with alkyl halide (R-X) to produce the desired sulfur-containing compounds of the present invention.

Another general method for the production of the desired sulfur-containing compounds of the present invention is outlined in the scheme of the following examples. In this scheme, dehydroepiandrosterone is protected (Example IV) with THP, and the protected compound is reacted (Example V) with Wittig reagent. Subsequent selective hydrogenation produces (Example VI) the corresponding ester which is deprotonated with LDA (or other suitable base) and alkylated with R-S-Ts (Example VII) resulting in the addition of the sulfur-containing side chain. Reduction of the sulfur-containing compound with lithium aluminum hydride yields (Example VIII) the corresponding alcohol. Subsequent removal of the C-20 hydroxyl with pyridine/-SO₃ complex (Example IX) followed by treatment with lithium hydride gives the protected sulfur-containing compounds which are part of the present invention. Standard deprotection (Example X) of these compounds yield the non-protected sulfur containing compounds.

EXAMPLE IV

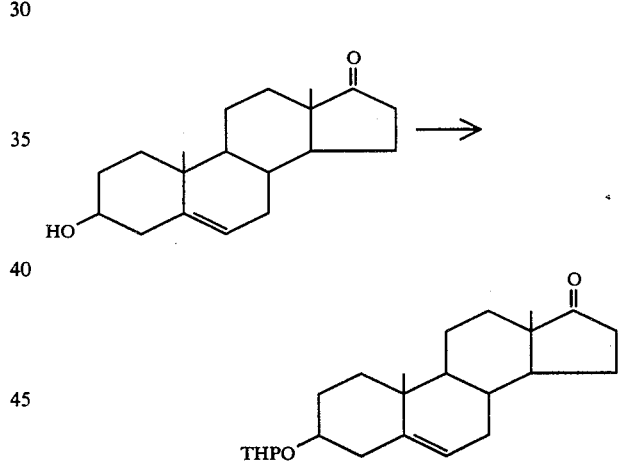

To a solution of 3-hydroxy androst-5-en-17-one (2.0 g, 3.47 mmole) in CH₂Cl₂ was added 5.0 ml of dihydropyran and a catalytic amount of pyridinium p-toluensulfonate (10 mg). The solution was washed with a solution of 1N NaOH, water and brine. Evaporation of solvent left a crude product which was recrystallized from 95% ethanol. (m.p 170°-172° C.).

EXAMPLE V

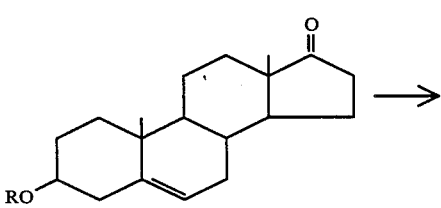

-continued

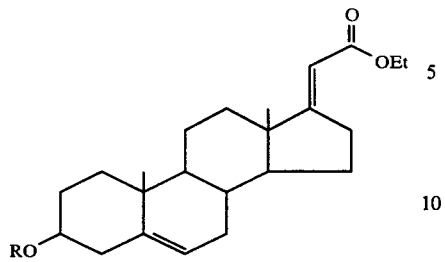

R=THP

A solution of the 3-tetrahydropyran-2-yloxyandrost-5-en-17-one (2.38 g, 6.39 mmole) and triethyl phosphonoacetate (4.29 g, 19.17 mmole) in anhydrous ethanol (50 ml) under nitrogen was treated slowly dropwise under stirring at 35°-40° C. with a solution of sodium ethoxide [prepared from sodium (440 mg. 19.17 mmole) in ethanol (10 ml)]. The mixture was refluxed for 18 hr and the reaction was followed by TLC. After cooling it was concentrated under reduced pressure, diluted with water and the product was extracted with ether. The solvent was evaporated and the residue was recrystallized from acetone-water to yield product: m.p. 128°-130° C.

EXAMPLE VI

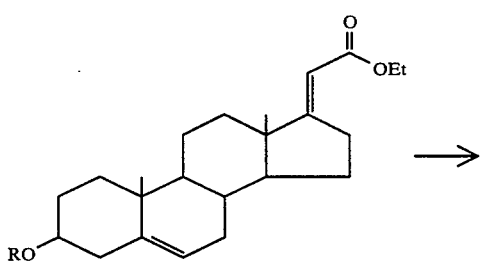

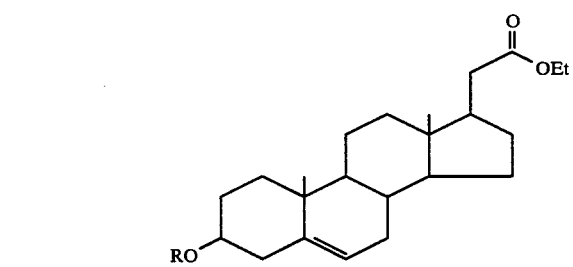

T=THP

Hydrogenation of steroid (313 mg, 0.7 mmole) in ethanol (100 ml) over pre-reduced platinum oxide (200 mg) was carried out at atmospheric pressure until the absorption of one equivalent of hydrogen was consumed (16.3 ml). The catalyst was removed by filtration through Celite. Concentration of the filtrate gave crude product which was recrystallized from acetone-water, m.p. 94°-95° C.

EXAMPLE VII

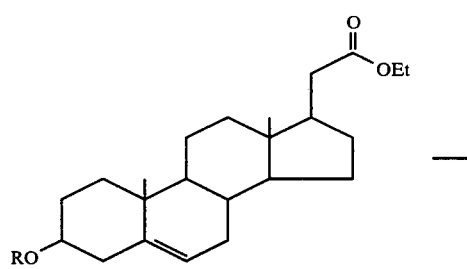

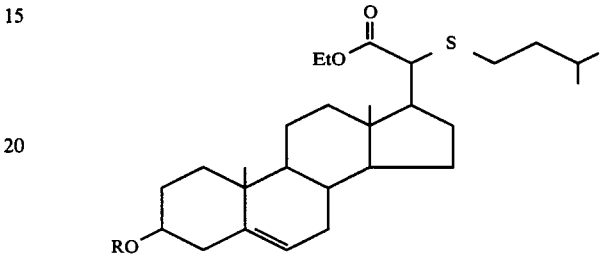

A solution of di-isopropylamine (0.05 ml. 0.3 mmole) in THF (3.0 ml) in a reactor fitted with a magnetic stirrer and a thermometer was cooled down to −30° C. A solution of n-butyllithium in n-hexane (0.14 ml, 0.3 mmole) was added by means of a syringe. After 20 min the contents of the reactor was cooled to −70° C. and a solution of the ster steroid (75.5 mg, 0.17 mmole) in THF (2.0 ml) was added dropwise maintaining the temperature below −70° C. After 45 min, a solution of isopentylthiotosylate (131.5 mg, 0.51 mmole) in THF (1.0 ml) and HMPA (0.5 ml) was added dropwise, maintaining the temperature at −70° C. The reaction mixture was further stirred at −70° C. and followed by TLC. The reaction was completed within 30 min. Ether was added until a precipitate appeared. It was quickly washed with water (three times). Evaporation of solvent left a jelly type of residue, which was recrystallized in acetone-water. m.p. 120°-122° C.

EXAMPLE VIII

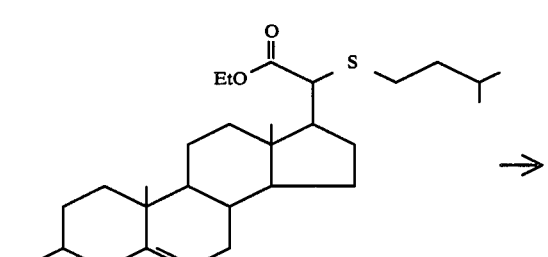

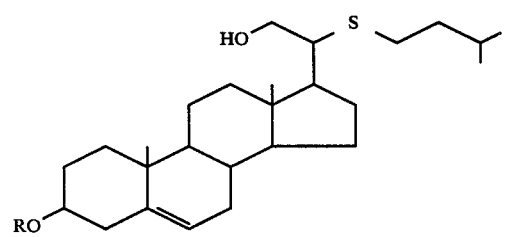

To a solution of steroid (91.7 mg. 0.16 mmole) in dry ether was added LiALH4 (excess) at room temperature. The reaction was stirred and followed by TLC. Upon completion of the excess of the reagent was decomposed by addition of saturated ammonium sulfate solution. The inorganic precipitate was removed by filtration and washed with ether. The combined ether solution was dried over NA2SO4 and upon evaporation of solvent yielded a crystalline product: m.p. 135°–136° C.

EXAMPLE IX

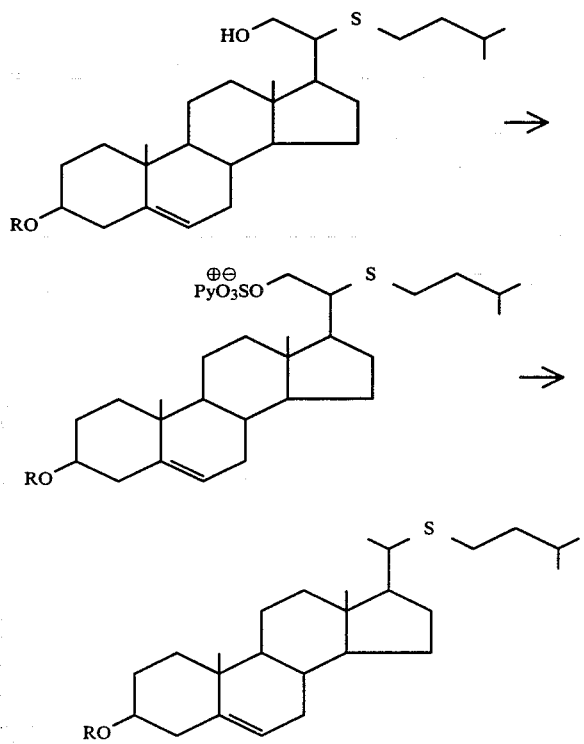

To a solution of hydroxysteroid 121 ml (0.24 mmole) in 5.0 ml of THF at −10° C. was added pyridine-sulfur trioxide complex (Aldrich). The reaction mixture was stirred at −10° C. followed by TLC until the reaction was completed (15 min). The reaction mixture was cooled to −20° C. and LAH was added in small portions. The suspension was further stirred for 30 min at −1° C. The reaction was quenched at −10° C. by adding a chilled solution of 10% NaOH dropwise until the reaction subsided. The precipitate was filtered and washed with ether. The ether filtrate was evaporated to produced protected product.

EXAMPLE X

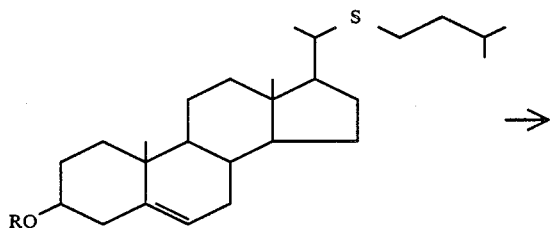

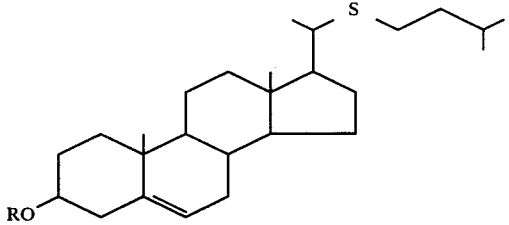

A solution of crude steroid in acetone (10 ml) with a catalytic amount of p-toluensulfonic acid was stirred at room temperature for 8 hr. The solvent was evaporated (rotavaporator). The residue was diluted with water and extracted with ether. The ether phase was washed with 5% NaOH, water and brine. The organic layer was dried over MgS)4 and evaporated to give crude product. Purfication by preparative TLC gave pure product.

The foregoing syntheses of the compounds of the present invention are illustrative, and many other conventional reactions and combinations of these reactions may be used to produce or to interconvert the compounds of the present invention. These conventional reactions and conditions may be found, for example, in any of the major organic or steroid chemical texts such as Fleser et al., "Steroids" (Reinholg, New York 1959); Kirk et al., "Steroid Reaction Rechanisms" (Elsevier, Amsterdam 1968); or Harrison et al., "Compendium of Organic Synthetic Methods" (Wiley-Interscience, New York 1971).

As mentioned previously, the compounds of the present invention are irreversible inhibitors of P-450 scc, and as such are useful in treating many clinical diseased involving excess hormone production. The activity of these compounds has been demonstrated by both chemical and biological—in primary cultures of rat, beef, and human adrenal cells—means.

As mentioned previously, the compounds of the present invention are potent inhibitors of the conversion of cholesterol to pregnenolone. In preincubation studies conducted in accordance with the protocol detailed in Example XI, for example, the trimethyl silyl-containing compound of the present invention showed a time-dependent loss of enzyme activity in the presence of NADPH and/or $O_2$ (suggesting that P-450 catalyzes at least one monoxygenation reaction in the conversion process prior to its inactivation—suggesting that TMS ethyl radicals may be generally useful as a new class of monoxygenase mechanism-based inhibitors). The results of these incubation studies are set forth in FIG. 1.

EXAMPLE XI

The final turnover mixture contained 2.5 μM adrenodoxin, 150 nM adrenodoxin reductase, 50 mM K+MOPS (pH 7.2), 10 mM $MgCl_2$, 0.2% Tween 20, 1 unit/mL catalase, a NADPH-generating system of 16 μM NADPH, 3 mM G6P, and 1 unit/mL G6P. For a typical preincubation experiment, inhibitor was added as an ethanol solution (2-10 mM) into the P-450 turnover mixture at 37° C. and the reactions were started by addition of NADPH stock solution. After, 0, 5, 10, 15, 30, or 45 min. of incubation, an aliquot of this mixture (200μ) was introduced into 1.8 ml of the turnover mixture containing [1, 2-$^3$H] cholesterol (100 μM 10,000 dpm/nmol). After 10 min., the reaction was terminated by acidification, and [4-¹⁴C] prengenolone were added as an internal standard. The resulting mixture was extracted using ethyl acetate and evaporated to dryness. The product pregnenolone was separated on silica gel TLC plates (Baker-flex) using 1:1 ethyl acetate-hexane as the solvent. The product formation was determined from the ratio of $^3H$ to $^{14}C$ in the recovered pregnenolone.

When rat adrenocortical cells were stimulated with ACTH in the presence of the P-450 scc inhibitors of the present invention, and the production of cortiscoterone measured, less corticosterone was produced in the presence of the compounds of the present invention, then when those compounds were absent.

This indicates that adrenal steroidogensis is inhibited, and most likely by the presence of the test compound. Corticosterone production rates by non-stimulated rat adrenal cell suspensions are approximately one-fifth those of ACTH stimulated rates. However, if cholesterol analogues with polar side-chains, such as 25 hydroxy cholesterol, are added to suspensions of non-stimulated cells, corticosterone production rate can be as much as one-half those of ACTH stimulated cells. From this it can be concluded that the polar side-chain cholesterol analogues have access to the P-450 scc under non-stimulating conditions, and that cholesterol probably does not. This property, combined with P-450 scc inhibitors with and without polar side chains was used to determine how ACTH stimulation results in increased conversion of endogenous cholesterol to corticosterone.

Effects of cholesterol analogues on adrenal cell corticosterone production are reported in the following table:

TABLE 2

Cells (30,000/ml) were preincubated with steroid for 10 minutes. Maximally stimulating levels of ACTH were then added and the incubation continued for another 60 minutes. The incubations were then quenched, and samples assayed for corticosterone fluorometrically.

| SAMPLE | CORTICOSTERONE PRODUCED (%) |
|---|---|
| ACTH only | 100 |
| ACTH + 20(S)22 thiacholesterol 2 ug/ml | 54.1 |
| ACTH + 20(R)22 thiacholesterol 2 ug/ml | 117.9 |
| ACTH + 25 hydroxycholesterol 2 ug/ml | 117.0 |
| 25 hydroxycholesterol 2 ug/ml | 21.9 |
| 25 hydroxycholesterol 5 ug/ml | 30.4 |
| 25 hydroxycholesterol 5 ug/ml + 20(S)22 thialcholesterol 5 ug/ml | 15.5 |

As can be seen, the addition of the 20(S)22thiacholesterol compouond of the present invention results in decreased corticosterone production.

Additionally data showing that the silicon and sulfur-containing compounds of the present invention are effective at halting steroid hormone biosynthesis when given at low concentrations to suspensions of human and rat adrenal cells are depicted in the following figures and table.

These data show that the cell suspensions respond to ACTH, as does the whole gland in intact animals, and that both the 22-thacholesterol and the 20-hydroxy-22(trimethylsilyl) pregnenedial (but not 22-thiaeipi-cholesterol nor 22 (trimethylisilyl) pregnenol) inhibits this ACTH-stimulated production of cortisol (humans) or corticosterone (rats). The data in Table 3 proves that the effect in cells is specific to the P-450 scc of those cells, not to a subsequent step in corticoid formation.

TABLE 3

Effect of Mechanism Based P-450scc Inhibitors on Corticosterone Production from 20a Hydroxycholesterol and Pregnenolone by Rat Adrenocortical Cells.

| 1st Incubation | 2nd Incubation | % Corticosterone Production During 2nd Incubation (ng/ml) | |
|---|---|---|---|
| 0.5% EtOH (control) | Pregnenolone | 100.0 | (266) |
| 20 OH 23 TMS | Pregnenolone | 87.0 | |
| 0.5% EtOH (control) | 20a Hydroxy-cholesterol | 100.0 | (70.4) |
| 20 OH TMS | 20a Hydroxy-cholesterol | 7.1 | |

20 OH 23 TMS = 20-(2-Trimethyl silyl ethyl)-pregnen-3, 20a-diol)

FIG. 1 shows the P-450 scc inhibition by the trimethylsilyl compound of the present invention. The P450 concentration was 1.35 $\mu M$ and the steroid was 20 $\mu M$ = NADPH; 0 = no inhibitor + NADPH; 0 = NADPH.

FIG. 2 shows the time and concentration dependence of 20-(2-Trimethyl silyl-ethyl) pregnen-3, 20a-diol (i.e., 20 OH TMS) effects on corticosterone production. Steroid was added at t = 10 min. Inhibition is strongly time dependent. At 10 $\mu M$ 20 OH TMS steroid, corticosterone production is obliterated by 40 min.

FIG. 3 shows time and concentration dependence of 20 (S) 22 Thiacholesterol effects on corticosterone production. Steroid was added at t = −10 min. Inhibition is strongly concentration dependent, but only slightly time dependent.

Figure 1:
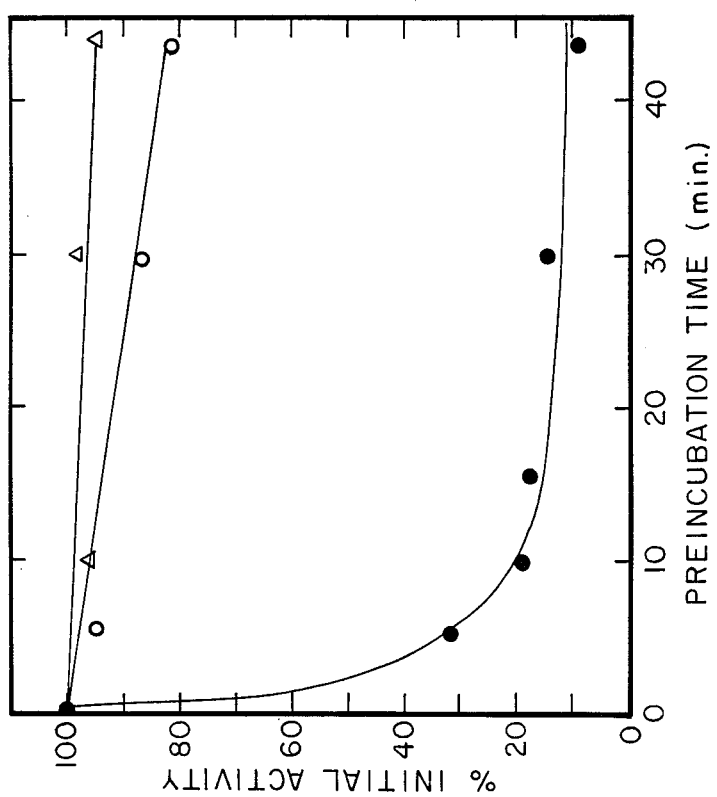
Figure 2:
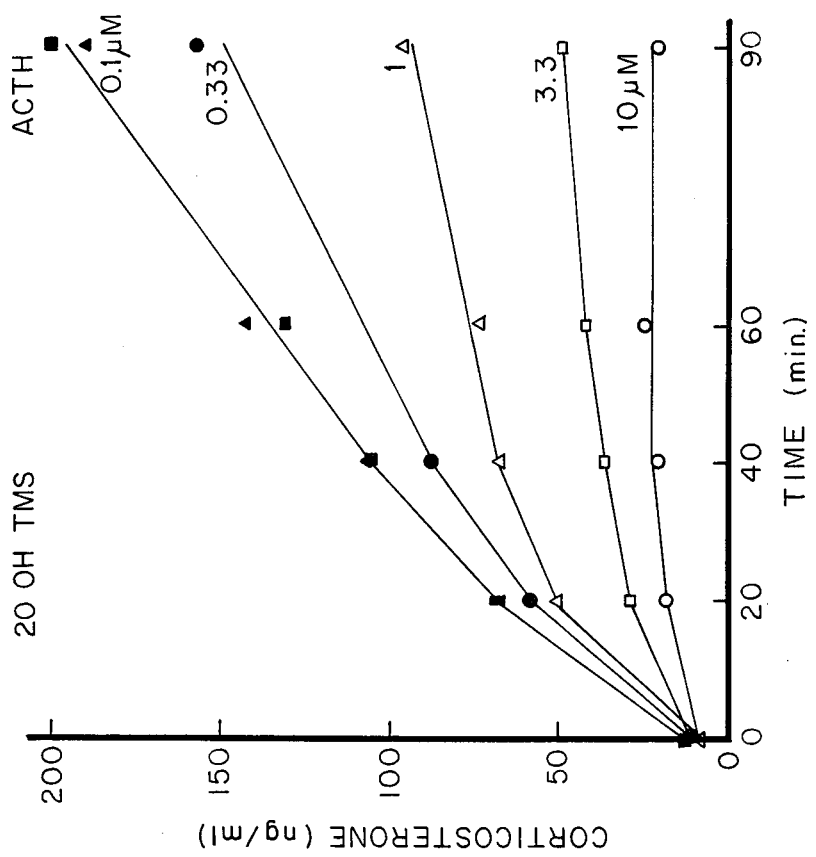
Figure 5:
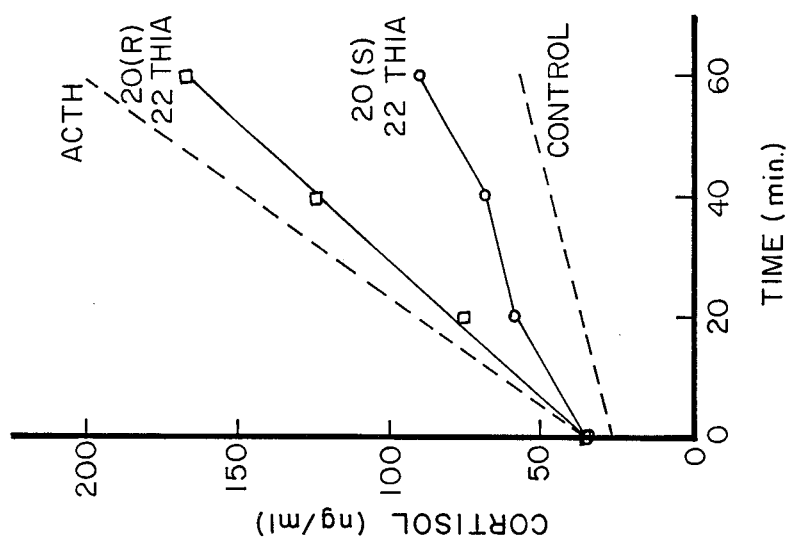
FIG. 5 shows that cortisol production is strongly inhibited by 10 $\mu M$ 20 (S) 22 Thiacholesterol (probably in a time dependent manner) and inhibited slightly by 20(R) 22 Thiacholesterol in a manner which is not time dependent.
Figure 4:
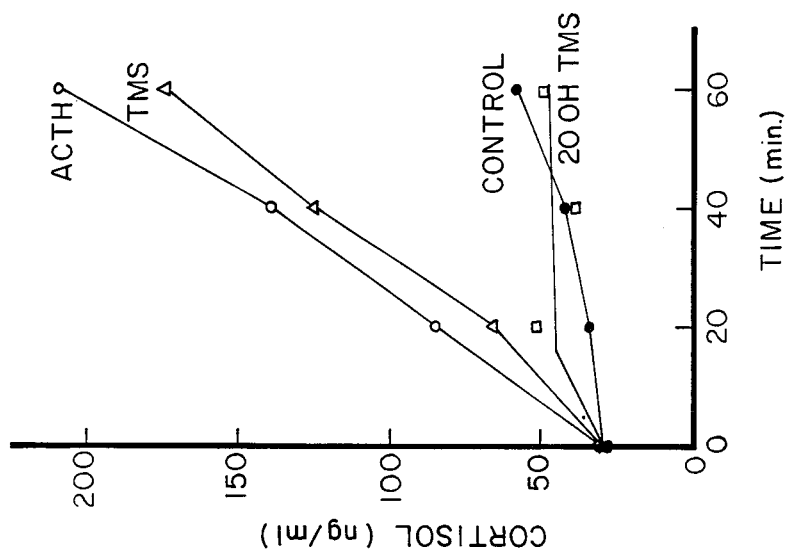
FIG. 4 shows that the 20 OH TMS steroid strongly inhibits cortisol production, probably in a time dependent manner, while the TMS steroid lacking a hydroxylated side chain has little inhibitory effect on cortisol production.
Figure 3:
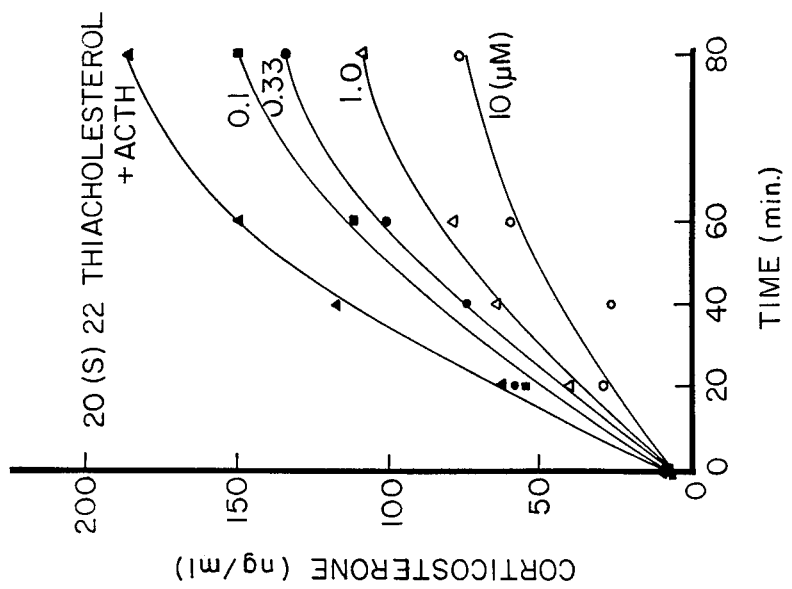

In view of this data, it can be concluded that the compounds of the present ivnention which contain either a sulfur or silicon atom in their side chains, would be useful as pharmaceutical preparations that would temporarily halt steroid hormone biosynthesis in a way beneficial to patients with certain hormone-related pathologies. Thus, in an aspect of the present invention there is provided a pharmaceutical composition comprising a sulfur or silicon-containing compound of the present invention as has been defined or a pharmaceutically acceptable salt thereof as an active ingredient together with any of the conventional pharmaceutically acceptable carriers or excipients.

The pharmaceutically acceptable salts of the compounds of the present invention may be prepared by conventional reactions with equivalent amounts of organic or inorganic solutions. As exemplary, but not limiting, of pharmaceutically acceptable salts are the salts of hydrochloric, hydrobromic, sulfuric, benzenesulphonic, acetic, fumaric, oxalic, malic and citric acids, and hydroxides of potassium and sodium, however, this list is by no means intended to limit the present invention to only this specific non-toxic and pharmaceutically acceptable salts.

The compositions may be administered parentally in combination with conventional injectable liquid carries such as sterile pyrogen-free water, sterile peroxide-free ethyl oleate, deydrated alcohol or propylene glycol. Conventional pharmaceutical adjuvants for injection solutions such as stabilizing agents, solubilizing agents and buffers, for example, ethanol, complex form agents such as ethylene diamine tetraacetic acid, tartrate and citrate buffers and high-moleculr weight polymers such as polyethylene oxide for viscosity regulation may be added. Such compositions may be injected intramuscularly, intraperitoneally, or intravenously. The compositions may also be formulated into orally administrable compositions containing one or more physiologically compatible carriers or excipients, and may be solid or liquid in form. These compositions may, if desired, contain conventional ingredients such as binding agents, for example, syrups, acacia, gelatin, sorbitol, tragacanth, or polyvinylpyrollidone; fillers, for exampoe, lactose, mannitol, starch, calcium, phosphate, sorbitol or methylcellulose; lubricants, for example, magnesium stearate, high-molecular weight polymers such as polyethylene glycols, high-molecular weight fatty acids such as stearic acid or silica; disintegrants, for example, starch; acceptable wetting agents as, for example, sodium lauryl sulfate. These compositions may take any convenient form, for example, tablets, capsules, lozenges, aqueous or oily suspensions, emulsions, or dry products suitable for reconstitution with water or other liquid medium before use. The liquid oral forms of administration may, of course, contain flavors; sweeteners; preservatives, for example, methyl or propyl p-hydroxybenzoates; suspending agents, for example, sorbitol, glucose or other sugar syrup, methyl, hydroxmethyl, or carboxymethyl celluloses, or gelatin; emulsifying agents as, for example, lecithin or sorbitan monooleate; or thickening agents. Non-aqueous compositions may also be formulated which comprise edible oils as, for example, fish-liver or vegetable oils. These liquid compositins may conveniently be encapsulated in, for example, gelatin capsules in a unit dosage amount.

The pharmaceutical compositions according to the present invention may also be administered, if appropriate, either topically as an aerosol or, formulated with conventionl bases, as a cream or ointment.

A particular aspect of the present invention comprises a compound of the present invention in an effect unit dose form. By "effective unit dose" is meant a predetermined amount sufficient to bring about the desired inhibitory effect.

And yet in a further aspect of the present invention, there is provided a method of producing an inhibitory effect on hormonal biosynthesis in mammals, including man, which comprises the administration of an effective inhibitory amount of a compound of the present invention or a pharmaceutically acceptable salt thereof to a mammalian host.

The dosage of the compounds of the active compounds of the present invention or their pharmaceutically acceptable salts will depend, of course, on the nature and severity of the bacterial infection of the mammalian host. Dosages of pharmaceutically active compounds such as those disclosed in the present invention are conventionally given in amounts sufficient to bring about the desired effect without causing undue burden upon the mammalian host.

Thus, while I have illustrated and described the preferred embodiment of my invention, it is to be understood that his invention is capable of variation and modification, and I therefore do not wish to be limited to the precise terms set forth, but desire to avail myself of such changes and alterations which may be made for adapting the invention to various usages and conditions. Accordingly, such changes and alterations are properly intended to be within the full range of equivalent, and therefore within the purview, of the following claims.

Having thus described my invention and the manner and process of making and using it, in such full, clear, concise, and exact terms so as to enable any person skilled in the art to which it pertains, or with which it is most nearly connected, to make and use the same:

I claim:

1. A method of irreversible inhibition of the enzymatic conversion of cholesterol to steroid hormones which comprises inactivating the P-450 scc enzyme responsible for conversion of cholesterol to progesterone with a compound of the formula:

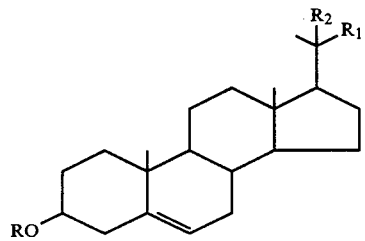

wherein R is hydrogen, $CH_3$, $PO(O^-)_2$, or other protecting group $R_2$ is hydrogen or hydroxyl; $R_1$ is $-S-R_3$ or $-CH_2CH_2Si(Ry)_3$ wherein $R_3$ is a $C_{1-6}$ straight chain alkyl, a $C_{1-6}$ straight chain alkylene, or a $C_{3-6}$ branched chain alkyl or alkylene, and wherein Ry is hydrogen, hydroxyl, $C_{-6}$ branched or straight chain alkyl, or mixtures thereof.

2. A method according to claim 1 wherein $R_1$ is $-S-R_3$.

3. A method according to claim 1 wherein $R_1$ is $-CH_2CH_2Si(Ry)_3$.

4. A compound of the formula

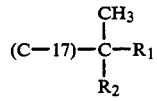

wherein $R_2$ is hydrogen or hydroxyl; $R_1$ is $-S-R_3$ or $-CH_2CH_2Si(Ry)_3$; wherein $R_3$ is $C_{1-6}$ straight or branched chain alkyl or alkylene; and wherein R is hydrogen, hydroxyl, $C_{1-6}$ branched or straight chain alkyls, or mixtures of the same, and wherein (C-17) is the C-17 position of a cholesterol tetracyclic ring system.

5. A pharmaceutical composition comprising a compound according to claim 4 or its pharmaceutically acceptable salt.

6. A compound of the general formula

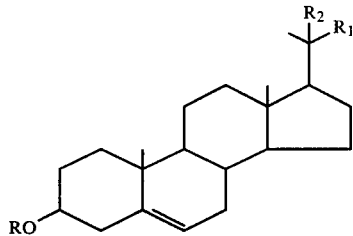

wherein R is hydrogen, $CH_3$, $PO(O^-)_2$, or other protecting group; $R_2$ is hydrogen or hydroxyl; $R_1$ is $-S-R_3$ or $-CH_2CH_2Si(Ry)_2$ wherein $R_3$ is a $C_{-6}$ straight chain alkyl, a $C_{1-6}$ straight chain alkylene, or a $C_{3-6}$ branched chain alkyl or alkylene, and wherein Ry is hydrogen, hydroxyl, $C_{1-6}$ branched or straight chain alkyl, or mixtures thereof.

7. The compound according to claim 6 wherein $R_1$ is $-S-R_3$.

8. The compound according to claim 6 wherein $R_1$ is $-CH_2CH_2Si(Ry)_3$.

* * * * *